(12) United States Patent
Peyman

(10) Patent No.: US 6,436,429 B1
(45) Date of Patent: Aug. 20, 2002

(54) PROCESS AND COMPOSITION FOR TEMPORARILY SUPPRESSING PAIN

(76) Inventor: Gholam A. Peyman, 8654 Pontchartrain Blvd., Unit #1, New Orleans, LA (US) 70124

( * ) Notice: Subject to any disclaimer, the term of this patent is extended or adjusted under 35 U.S.C. 154(b) by 0 days.

(21) Appl. No.: 09/475,473

(22) Filed: Dec. 30, 1999

Related U.S. Application Data

(63) Continuation-in-part of application No. 09/340,111, filed on Jun. 28, 1999.

(51) Int. Cl.$^7$ .............................. A61K 7/16; A61K 9/68; A61F 13/00; A61F 2/00
(52) U.S. Cl. ........................... 424/435; 424/48; 424/49; 424/434; 424/427
(58) Field of Search ................................ 424/427, 434, 424/49, 435, 48

(56) References Cited

U.S. PATENT DOCUMENTS

| | | | |
|---|---|---|---|
| 4,277,464 A | 7/1981 | Reussner et al. | 424/177 |
| 4,291,017 A | 9/1981 | Beierle et al. | 424/52 |
| 4,291,045 A | 9/1981 | Mackay et al. | 424/270 |
| 4,497,835 A | 2/1985 | Winston | 426/72 |
| 4,554,167 A | 11/1985 | Sorge et al. | 426/285 |
| 4,627,980 A | 12/1986 | Lynch | 424/54 |
| 4,980,152 A | 12/1990 | Frazier et al. | 424/52 |
| 5,114,726 A | 5/1992 | Tsau et al. | 426/289 |
| 5,122,365 A | 6/1992 | Murayama | 424/49 |
| 5,686,064 A | 11/1997 | Gaffar et al. | 424/57 |
| 5,698,215 A | 12/1997 | Kalili et al. | 424/440 |
| 5,709,873 A | 1/1998 | Bar-Shalom et al. | 424/422 |
| 5,728,397 A | 3/1998 | Fuisz | 424/439 |
| 5,736,175 A | 4/1998 | Cea et al. | 426/6 |
| 5,756,107 A | 5/1998 | Hahn et al. | 424/401 |
| 5,824,292 A | 10/1998 | Carr et al. | 424/49 |
| 5,858,391 A | 1/1999 | Cuca et al. | 424/439 |
| 5,866,179 A | 2/1999 | Testa | 426/3 |
| 5,912,274 A | 6/1999 | Stringer et al. | 514/731 |

*Primary Examiner*—Thurman K. Page
*Assistant Examiner*—Amy E. Pulliam
(74) *Attorney, Agent, or Firm*—Roylance, Abrams, Berdo & Goodman, L.L.P.

(57) ABSTRACT

A composition and process for suppressing pain and irritation of tissue includes an anti-irritant in an effective amount to suppress pain and irritation temporarily when applied topically to the skin or mucosa. The anti-irritant is a natural or non-nutritive sweetener. The composition can be a solid containing an edible acid such as citric acid and ascorbic acid from fresh lemon juice to form a solution having a pH of about 2.0 to 4.0 and an anti-irritant, such as sodium saccharine. The composition can be used to apply a pharmaceutical agent to the skin, mucosa or eye without irritation. The acidic composition can further be used to remove or loosen calculus deposits from the teeth without burning or irritation of the gums.

12 Claims, No Drawings

PROCESS AND COMPOSITION FOR TEMPORARILY SUPPRESSING PAIN

CROSS-REFERENCE TO RELATED APPLICATION

This application is a continuation-in-part of application Ser. No. 09/340,111, filed Jun. 28, 1999 by Peyman and is hereby incorporated by reference in its entirety.

FIELD OF THE INVENTION

The present invention is directed to a process and composition for treating the surface of the skin or other tissue with an active compound substantially without irritation. More particularly, the invention is directed to a process and composition for suppressing pain topically on the eye, skin or mucosa tissue.

BACKGROUND OF THE INVENTION

Many substances are commonly applied to the skin, mucosa tissue and to other tissue of humans and animals to treat the surface of the skin or tissue. Typical examples of compositions that are applied to the skin include cosmetics, sunscreens and the like. Other compositions often include a pharmaceutical agent such as an antibiotic or bactericide for treating the surface of the tissue.

Topically applied compositions are generally in the form of liquids, creams, lotions and gels. In many instances, the compositions that are applied topically contain various components, which inherently cause irritation and inflammation when applied to the skin or the mucosa. The occurrence and frequency of the irritation can vary depending on the person, the specific components in the composition and the various components present.

Common symptoms of irritation from topically applied compositions include itching, stinging, burning, tingling, tightness, redness and swelling. The irritation can be due to the direct effect on the skin or the mucosa of the active ingredient or the carrier or in response to the immune system directly toward the chemicals alone or in combination with the skin components.

Many ingredients used in topically applied products are known irritants or are potentially irritating, especially for certain people with some allergies or sensitivities. Ingredients which can act as irritants include solvents, fragrances, preservatives, propellants, and pharmaceutical agents. Examples of common topical compositions, which can cause irritation, include exfolients and skin renewal agents, antiperspirants, antihistamines, anti-inflammatory agents, skin protective agents, insect repellants and sunscreens. Where more than one irritant compound is present, the effects can be additive. In addition, various components can interact with each other to cause irritation which might not occur when used alone.

Various efforts have been proposed to attempt to find methods and compositions for reducing or eliminating irritation caused by the topical application of various compositions. For example, one such method attempts to reduce the irritation caused by hydroxy acids and keto-acids in topically applied products by adding a strong alkali base metal such as sodium or potassium hydroxide. The effect of the hydroxide is to raise the pH and to reduce the acidity of the composition. However, this approach has the disadvantage of reducing the effectiveness of the hydroxy acid to penetrate the skin and to reduce the effectiveness of the acid. Other hydroxides and organic amines have also been proposed to adjust the pH of the composition. However, raising the pH using these bases also reduces the effectiveness of the composition.

A further example of methods reducing irritation caused by topically applied compositions is disclosed ion U.S. Pat. No. 5,716,625 to Hahn. This patent discloses the use of a strontium metal cation to reduce irritation. It is proposed that the cation interacts with the epidermis nerve cells to prevent or counteract the sensation of irritation by interfering with the irritation inducing components of the skin cells. The strontium cation is proposed to alter the ability of the epidermal cells to depolarize by blocking or interfering with ion channel or pump operation or by altering the transmembranal action potential. It has also been proposed that the strontium cation acts to inhibit or modify the action of skin cell protease or other irritation inducing components.

The human skin and mucosa tissue presents a complicated structural and sensory environment. The skin contains nerves and highly specific sensory cells that are specialized. These cells are developed to differentiate the stimuli leading to specific sensation such as pain. In addition, nerves in the skin are responsive to native or foreign chemicals such as proteases, prostaglandins, complement system molecules, allergens and the like. Agents that are effective in combating one stimulus are often ineffective against another stimulus.

Many pharmaceutical agents when applied topically produce a burning sensation, especially when applied to a cut or sensitive tissue. For example, various eye drops containing a pharmaceutical agent when applied to the eye result in a painful burning of the eye.

Accordingly, there is a continuing need in the industry for a method of reducing or eliminating the pain associated with the topical application of various components.

SUMMARY OF THE INVENTION

The present invention is directed to a process and composition for inhibiting pain and irritation that is normally caused by topically applying a bioactive agent or medicament. More particularly, the invention is directed to a process for treating tissue with a liquid or solid composition and temporarily suppressing pain of the tissue being treated.

Accordingly, a primary object of the invention is to provide a process for treating skin or mucosa tissue with a composition where the composition contains an active ingredient and an effective amount of an anti-irritant.

Another object of the invention is to provide a process for treating tissue by contacting said tissue with a composition comprising a water soluble carrier, an effective amount of a bioactive agent, and anti-irritant to temporarily suppress pain and irritation of the tissue.

A still further object of the invention is to provide a process for topically treating mucosa with a water soluble solid composition containing a pharmaceutical agent and an effective amount of an anti-irritant.

Another object of the invention is to provide a process for temporarily suppressing pain and irritation by topically applying a solid composition containing an effective amount of an anti-irritant.

A further object of the invention is to provide a process and composition for removing calculus from tooth surfaces substantially without irritation to the gums and the tooth by applying a solid composition containing an acidic or alkaline material and an effective amount of an anti-irritant.

Another object of the invention is to provide a solid composition containing an active component for applying topically to the skin or mucosa, where the composition contains a pain suppressing amount of saccharine.

A further object of the invention is to provide a process for topically treating skin or mucosa with a water soluble solid composition capable of forming a solution having a pH of about 4.0 or less and a pain and irritation suppressing amount of a synthetic sweetener.

The objects and advantages of the invention are basically attained by providing a process for treating tissue of an animal with at least one bioactive compound by providing a water soluble composition comprising, at least one bioactive compound and at least one sweetener. The sweetener is included in an effective amount to block pain receptors temporarily in animal tissue upon release from the composition. The composition is applied to the tissue of the animal in an effective amount to treat the tissue with the bioactive compound and to suppress pain and irritation of the tissue.

The objects of the invention are further attained by providing a process for removing calculus and other deposits from the surface of the teeth of an animal comprising the steps of: providing a water soluble composition containing an edible acid in an amount to form a solution having a pH of about 6.0 or less and at least one sweetener in an amount to suppress irritation of gum tissue. The water soluble composition is placed in the mouth or applied to the surfaces of the teeth for an effective amount of time to substantially remove calculus and deposits from the teeth.

The objects and advantages of the invention are also attained by providing a process for temporarily suppressing pain receptors and reducing irritation of the tissue of an animal comprising the steps of: providing a solid or semi-solid carrier, at least one water soluble or water dispersible bioactive compound and at least one sweetener. The sweetener is present in an effective amount to suppress the pain receptors of the tissue and to reduce pain and irritation to the tissue caused by the composition. The tissue is contacted with the bioactive compound in an amount to treat the tissue with the bioactive compound substantially without irritation to the tissue.

The objects of the invention are further attained by providing a composition comprising a solid or semi-solid carrier, at least one bioactive component and a pain and irritation suppressing amount of a non-nutritive sweetener.

The objects, advantages and other salient features of the invention will become apparent from the following detailed description of the invention.

DETAILED DESCRIPTION OF THE INVENTION

The present invention is directed to a process and composition for temporarily suppressing pain and irritation by applying an effective amount of an anti-irritant to the skin, mucosa, eye or other tissue. More particularly, the invention is directed to a process and composition for topically delivering a composition to a specific site on a patient where the composition contains an anti-irritant in an amount to inhibit irritation to the delivery site.

The composition of the invention in preferred embodiments contains at least one active component such as a biologically active agent, a suitable vehicle or carrier, and an anti-irritant. The carrier can be a liquid, solid or semi-solid. In various embodiments, the composition is an aqueous solution. Alternatively, the composition can be a dispersion, emulsion, gel, lotion or cream containing a vehicle for the various components. In one embodiment, the primary vehicle is water. The liquid vehicle can include other materials, such as alcohols, glycerin, and mineral oils with various emulsifiers or dispersing agents as known in the art to obtain the desired consistency and viscosity.

The composition that is applied to the treatment site can be a liquid or solid depending on the treatment site. For example, the composition can include a solid or semi-solid carrier when the composition is used as a lozenge or tablet for the oral delivery of an active component. In further embodiments the composition can be used as an implant or a suppository. Liquid carriers are desirable in some instances for oral use, such as mouth washes, gargle solutions and the like. Liquid carriers are also desirable for irrigation solutions for irrigating a cut, wound or surgical site, such as during surgical removal of a tumor and irrigating the bladder or vagina.

The invention is primarily directed to a composition containing an anti-irritant agent in an effective amount that is capable of suppressing the pain receptors in the tissue to inhibit pain and irritation to the area being treated topically with the composition. The invention is further directed to a process of treating tissue or applying an active agent to an area with little or no irritation. It has been found that various natural and particularly artificial or synthetic non-nutritive sweeteners are able to provide a temporary suppression of pain and irritation to the area being treated when applied topically. In particular, it has been found that compositions using an artificial, non-nutritive sweetener in amounts in excess of the amounts conventionally used for sweetening a food product have an anti-irritant effect. Although not completely understood, it is believed that the natural sweeteners and particularly the synthetic, non-nutritive sweeteners are able to block the pain receptors at the site on the tissue being treated. Patients using the compositions of the invention, when applied topically to skin, mucosa, and other tissue, experience a reduction in pain and irritation than would otherwise occur and without numbness or loss of feeling to the treated area.

In preferred embodiments of the invention, the anti-irritant is an artificial non-nutritive sweetener included in the composition in an effective amount to suppress or inhibit pain and inhibit irritation caused by topically applying the composition to the skin, mucosa or other tissue. The artificial, non-nutritive sweetener can be a commercially available sweetener such as saccharine and the salts thereof, aspartame, cyclamates and the salts thereof, acetesulfone K, and mixtures thereof. In preferred embodiments, the non-nutritive sweetener is sodium saccharine obtained commercially as a food sweetener, such as the product available under the trademark Sweet-N-Low. The commercially available food sweeteners typically include a bulking and dispersing component such as dextrose. The bulking and dispersing components of the commercial sweeteners do not interfere with the anti-irritant effect of the sweetener. Sodium saccharine is generally preferred since it is readily soluble in water and readily available.

In further embodiments, the anti-irritant is a natural sweetener such as a monosaccharide, disaccharide or polysaccharide. Suitable natural monosaccharide sweeteners include glucose and fructose. Other sweeteners include, arabinose, xylose, ribose, mannose, galactose, dextrose, sorbose, sorbitol, mannitol, and mixtures thereof. Suitable disaccharides include, sucrose, lactose, maltose and cellobiose. The polysaccharides can include partially hydrolyzed starch, dextrin, stevioside or corn syrup salts. In embodiments of the invention, the natural sweeteners can be used in combination with one or more non-nutritive sweeteners. Other suitable sweeteners include sorbitol, mannitol, xylitol and the like.

The composition of the invention includes a carrier capable of delivering the anti-irritant and the active ingredient. Generally, the preferred liquid carrier is water, although other pharmaceutically acceptable carriers can be used depending on the intended use of the composition. The carrier can include various co-solvents, dispersing agents or emulsifiers as known in the art. In one embodiment, the carrier is water substantially in the absence of emulsifiers or dispersing agents. Alternatively, the carrier can also contain various thickening or gelling agents to obtain the desired consistency or viscosity.

In embodiments of the invention, the vehicle for topical application to the skin can include various alcohols, glycols such as glycerin, lipid materials such as fatty acids, mineral oils, phosphoglycerides, collagen, gelatin and silicone based materials. The vehicles used for compositions for treating mucosa are limited primarily by the toxicity of the vehicle to the tissue.

The anti-irritant is preferably dissolved or dispersed in the liquid carrier in an amount to provide the desired anti-irritant effect. The amount of the anti-irritant will depend on the particular anti-irritant being used, and the active ingredient responsible for the irritation since some active ingredients are more likely to cause irritation. The sensitivity of the intended tissue being treated also determines the amount of the anti-irritant in the composition.

In one embodiment of the invention, the anti-irritant is an artificial sweetener. A particularly suitable sweetener is the commercially available sodium saccharine. The sodium saccharine is included in the amount of about 10% to about 40% by weight based on the total weight of the carrier. The amount of the non-nutritive can vary depending on the other components of the composition. Generally, the non-nutritive sweetener is used in similar amounts for liquid and solid carriers. Generally, the sodium saccharine is included in the amount of 15% to about 30% by weight based on the total weight of the carrier. Commercially available saccharine products sold as ready-to-use sugar substitutes contain about 60% by weight saccharine, with the remaining amount being made up of dextrose and other bulking, dispersing and anti-caking agents. These commercially available sodium saccharine products are used in amounts, typically about 25% to 35% by weight, to provide the desired saccharine concentrations in the final product. Other artificial non-nutritive sweeteners such as aspartame and cyclamates and salts thereof are used in similar amounts as the saccharine. In further embodiments, the artificial non-nutritive sweetener is included in an amount to form a saturated solution.

The natural sweeteners, such as sucrose, can be included in the composition in the amount of about 15% to 30% by weight based on the total weight of the composition. Generally, when the carrier is a liquid the natural sweetener forms a saturated or near saturated solution. In preferred embodiments, the anti-irritant is an artificial non-nutritive sweetener to avoid the stickiness associated with topical applications of natural sweeteners. In still further embodiments the composition is an aqueous medium containing a mixture of a natural sweetener, such as sucrose or sorbitol, and an anti-irritant amount of a synthetic sweetener such as sodium saccharine.

The composition also contains an active compound which can be at least one bioactive ingredient in an amount to provide effective treatment of the patient in need thereof. The bioactive ingredient can be, for example, an antifungal, anti-inflammatory, antibiotic, analgesic, immunosuppressive agent, and mixtures thereof. The anti-inflammatory agents can be steroidal, non-steroidal or salicylates. Examples of anti-inflammatory agents include acetylsalicylic acid (aspirin), ibuprofen and acetaminophen. The suitable antibiotics can include aminoglycosides, cephalosporins, macrolides, monobactrams, penicillins, quinolines, sulfonamides and tetracyclines as known in the art. Examples of immunosuppressive agents include cyclosporin, azathioprine and $Rh_o(D)$immune globulin. These active ingredients are intended to be exemplary of suitable pharmaceutically active components. It will be understood that other bioactive ingredients can be used that are capable of inducing a desired response or treating a particular condition. The amounts of the active compounds in the composition are standard concentrations for topically applied components as known in the art.

In further embodiments, the composition includes a pharmaceutically acceptable or edible acid to adjust the pH below 7.0, and generally below about pH 6.0. Suitable acids include, for example, citric acid, acetic acid, ascorbic acid, malic acid, adipic acid, fumaric acid, and mixtures thereof. In embodiments of the invention, the acid functions as a bioactive compound for certain topical applications. In preferred embodiments, the acid is in the form of a citrus juice from lemons, limes, oranges, grapefruits, tangerines, tangelos, and mixtures thereof. Generally, the citrus juice is fresh squeezed juice or juice obtained from reconstituted concentrate. The most preferred citrus juice is fresh lemon juice. In further embodiments, the composition can contain a mixture of citric acid and ascorbic acid.

In embodiments of the invention, the acid, which can be a citrus juice, is included in an amount to provide a solution having a pH of about 2.0–6.0, depending on the desired pH for the tissue being treated. In embodiments, the composition has a pH of about 2.0–3.0 for some topical applications to the skin and mucosa. Fresh lemon juice, for example, typically has a pH of about 2.3 to 2.4. In embodiments where the carrier is a liquid, the acid compound is included in an amount to produce a solution having a pH of about 2.0–6.0, and preferably a pH of about 2.0–5.0.

Acidic agents are known generally to produce a burning and irritating effect when applied to sensitive tissue such as scratches or cuts on the skin, mucosa and the eye. It has been found that the anti-irritants of the invention, and particularly sodium saccharine, has an anti-irritant effect on tissue to inhibit the irritation caused by the acid added in an effective amount. Moreover, pH measurements of acid solutions containing varying amounts of sucrose and/or sodium saccharine have shown that the sucrose and sodium saccharine do not significantly alter the pH of the acidic solution. One aspect of the invention is based on the use of an anti-irritant agent without significantly adjusting the pH of the acidic solution.

In embodiments of the invention, the pH of the composition is adjusted as necessary to dissolve a desired active compound. For example, certain compounds are stable or soluble only in acid or alkaline solutions and cannot be easily dissolved without adjusting the pH. The anti-irritant of the invention enables the use of acidic or alkaline solutions containing compounds that are insoluble or unstable at neutral pH without irritation normally associated with acidic or alkaline solutions. In one embodiment, acid solutions having a pH of less than about 5.0 can be applied to the skin or mucosa tissue substantially without irritation.

The composition in one form of the invention is an aqueous solution containing an active ingredient for applying topically to the skin, mucosa, or other tissue. Compositions for applying topically to the tissue preferably contain an antibiotic, antibacterial agent, analgesic or anti-inflammatory, and an anti-irritating amount of a natural or artificial sweetener. The composition is particularly suitable for treating minor cuts, scratches, and abrasions on the skin substantially without irritation. It has been found that an aqueous solution containing 25% to 35% by weight sodium saccharine and an acid, such as ascorbic, citric or acetic acid to produce a solution having a pH of about 2.5–3.0, can be applied to scratches and minor cuts on the skin substantially without irritation. The sodium saccharine is believed to provide a temporary suppression of the nerve endings on the skin to prevent or reduce the irritation. It has also found that lemon juice having a pH of about 2.5 containing about 30% by weight sodium saccharine can be applied to minor skin cuts substantially without the irritation normally associated with an acidic solution applied to a cut.

In a further embodiment, the composition is an aqueous ophthalmic preparation for treating the eyes where the preparation contains an effective amount of an anti-irritant. Generally, the ophthalmic preparation is an aqueous solution diluted to the desired concentration with a physiological saline solution containing potassium chloride, sodium chloride and glucose. In further embodiments, the ophthalmic preparation is a lactated Ringer's solution. The ophthalmic preparation can be administered in the form of drops to the eye to reduce the discomfort associated with dryness and to aid in the healing of injured conjunctival and corneal tissue. The solution can contain a suitable buffering agent, surfactant and an anti-irritant amount of a natural or non-nutritive sweetener. The ophthalmic solution preferably contains at least one pharmaceutical agent.

The buffering agent is a pharmaceutically acceptable component to adjust the pH of the solution in the desired range. Suitable buffering agents include the combination of citric acid and a citrate. Other acids such as lactic, maleic and succinic acid can be used. Phosphate salts such as monosodium dihydrogenphosphate, disodium monohydrogenphosphate, monopotassium dihydrogenphosphate, dipotassium monohydrogenphosphate, and mixtures thereof can also be used. The surfactants can be, for example, polyoxyalkylene derivatives such as the surfactants sold under the trademarks Tween-80, Tween-60 and Tween-40. The ophthalmic composition generally is adjusted to a pH of about 6.0–7.0. In further embodiments, the pH can be adjusted to below 6.0 without irritation.

The ophthalmic preparation preferably contains about 15% to 30% by weight of a non-nutritive sweetener to serve as an anti-irritant based on the weight of the carrier. Sodium saccharine is the preferred anti-irritant for use in ophthalmic preparations. The ophthalmic preparation preferably includes a pharmaceutical agent in standard amounts commonly delivered to the eye by topical application. The preparation is generally applied to the eye or ocular cavity by applying drops to the surface of the eye. The ophthalmic preparation preferably includes a pharmaceutical agent or active compound commonly used in ophthalmic solutions. For example, the ophthalmic solution can contain an anti-inflammatory agent, antibiotic, vasoconstrictor, antifungal, or the like, in conventional concentrations.

In a further form of the invention, the composition is an irrigating solution for use in a process of irrigating a surgical site, such as an ocular cavity or in the eye to replace the vitreous humor. For example, during ocular surgery, an aqueous solution of a saccharide or disaccharide is supplied to the ocular cavity or into the eye ball to irrigate the cavity and support the eye ball during surgery. The aqueous solution can also include an anti-irritating amount of a synthetic sweetener. The surgical irrigating solution is an aqueous solution and generally contains about 15% to about 35% by weight of an artificial sweetener based on the weight of the carrier.

In a further embodiment of the invention, the composition is an oral composition effective in removing plaque and calculus deposits from the surface of teeth. Calculus deposits are generally formed of calcium phosphate and calcium carbonate that adhere to the tooth surfaces and are typically associated with inflammation and bleeding of the gums. Calculus deposits are frequently a primary cause of receding gums.

The oral composition in one embodiment of the invention is an aqueous solution containing an edible acid and an anti-irritant. The oral composition can be used as a mouthwash or rinse or as a dentifrice in combination with brushing or other mechanical cleaning of the teeth. The edible acids generally include, for example, citric acid, ascorbic acid, acetic acid, tartaric acid, maleic acid, fumaric acid, and mixtures thereof. The acid is included in an amount to provide a pH of less than 7.0, and generally about 2.0 to 6.0, and preferably about pH 5.5 to 6.0. In a preferred embodiment, the oral composition is fresh lemon juice. In an embodiment, the oral composition has a pH of about 3.0–4.0. In further embodiments, the oral composition contains a mixture of citric acid and ascorbic acid in amounts to provide a pH of less than 6.0 and generally about 5.5 to 6.0.

The anti-irritant in the oral composition is preferably an artificial or natural sweetener. The preferred anti-irritant is sodium saccharine, aspartame or cyclamates, in the amount of about 15% to 30% by weight. Alternatively, the anti-irritant can be sorbitol, mannitol, xylitol, and maltitol or mixtures thereof. The composition further contains a mixture of an artificial sweetener and a natural sweetener. Generally, the disaccharide are less preferred for oral rinses to minimize the plaque formation. In further embodiments, the oral composition can contain a flavoring agent, a fluoride source, anti-carrier agent, antibacterial agent, humectant, emulsifier, bleaching agent, surfactant or solubilizing agent. Although the oral composition is preferably an aqueous solution, the solution can contain up to 20% by weight of a cosolvent, such as ethyl alcohol.

Suitable flavoring agents include natural or synthetic flavors or oils. The natural flavors include citrus oils, such as lemon oil, lime oil, grapefruit oil, fruit essences, peppermint oil, spearmint oil, clove oil, bay oil, eucalyptus oil, cinnamon oil, and wintergreen oil.

In embodiments of the invention, the oral composition is preferably an aqueous composition applied to the tooth surface either alone or in combination with mechanical application. In one embodiment of the invention, the oral composition contains fresh lemon juice and sodium saccharine having a pH of about 2.0 to 4.0. This oral composition is applied to the calculus deposits with a soft dental brush or proxy brush to brush the composition onto the calculus deposits and between the teeth for a sufficient amount of time to remove or loosen the calculus deposits. Generally, the oral composition is applied followed by neutralizing the acid in the mouth and on the tooth surface. Neutralizing the acids can be by rinsing with water or other mouth rinse to wash and remove the acid from the tooth surfaces. Alternatively, a commercially available dentifrice, such as tooth paste, can be used by brushing to neutralize and remove the acid from the tooth surfaces.

Typically, the oral composition at a pH of about 2.0–4.0 effectively removes or loosens the calculus deposits without the need for mechanical abrasion or cleaning. The composition for applying directly to the tooth surfaces can include a pH adjusting agent or buffer to raise the pH to at least 5.0, and alternatively to at least pH 5.5, to reduce the effects of the acid on the enamel and dentin surfaces of the tooth.

Regular cleaning of the tooth surfaces with the oral composition has shown to remove substantial amounts of calculus deposits on the teeth and to loosen the deposits. In some instances, the calculus deposits are completely removed. In other instances, the deposits are loosened so that they can be easily removed by a dentist or hygienist during routine cleaning by mechanical action. The composition is also found to be effective in preventing or reducing the amount of the calculus deposits which normally form on the teeth. A suitable oral composition is an aqueous solution containing an edible acid in an amount to provide a pH of about 2.0 to 6.0, generally about pH 5.5 to 6.0, and about 20% to about 30% by weight of an anti-irritant, such as sodium saccharine.

In a further embodiment, the oral composition can contain a physiologically acceptable alkaline agent to form a solution having a pH greater than 7. Examples of suitable alkaline agents include carbonates and bicarbonates such as sodium bicarbonate. Compositions containing sodium bicarbonate can be used as an oral rinse or an aid during the brushing of the teeth. In preferred embodiments, the oral composition contains an artificial sweetener in an effective amount to avoid or reduce irritation to the mouth, teeth and gums.

In another embodiment, the carrier is a solid and the composition is in a tablet or lollipop form that can be placed in the mouth to dissolve for treating the mouth, teeth and gums. For example, a tablet can be produced from a water soluble carrier containing a mixture of an acidic agent for treating of the teeth and gums, and an effective amount of an anti-irritant. Alternatively, a tablet can be formed containing an anti-inflammatory, such as aspirin, and an anti-irritant where the tablet can be chewed or swallowed. The anti-irritant reduces the irritation to the stomach normally experienced by aspirin and other bioactive compounds. In further embodiments the composition includes a water soluble carrier, an alkaline agent and an anti-irritant.

In embodiments of the invention, the carrier is solid or semi-solid at room temperature that is able to release the active components and anti-irritant to the delivery area. In embodiments of the invention, suitable solid carriers included sucrose, corn syrup solids, and other confectionery compositions. In embodiments, the carrier is a lozenge, hard candy, lollipop or gel and the like comprising a mixture of a natural sweetener and an artificial sweetener such as sodium saccharine and at least one active component. Preferably, the solid carrier is water soluble that can dissolve in the mouth to release the active agent and anti-irritant. Preferred natural sweeteners include sorbitol, mannitol and xylitol.

Examples of semi-solid carriers include gels, chewing gums and other chewable compositions and compositions as known in the art. The carrier can be a conventional toothpaste or dentifrice gel. In one embodiment of the invention, the composition is in the form of a chewing gum comprising a chewing gum base, an active component and a sweetener in an amount to provide an anti-irritant effect. The active component can be an analgesic, such as aspirin, acetomemophen or ibuprophen, and the anti-irritant can be an artificial sweetener, such as sodium saccharine. Oral compositions preferably contain an effective amount of a fluoride to treat the tooth surfaces.

The chewing gum base of the invention can be a conventional gum base as known in art that can contain one or more solvents, plasticizer, favorants and colorants. The composition generally contains up to about 50% by weight of a gum base based on the total weight of the composition. Suitable chewing gum bases include natural and synthetic elastomers and rubbers. Natural chewing gum bases include natural rubber, chickle, jeluting, gutta percha and croun gum. Other gum bases includes rosins, such as comatone resin, pontianak resin, copel gum, kauri gum, dammar gum, sweet bay gum, spruce gum, and balsams. Synthetic elastomers includes butadiene-styrene copolymers, isobutylene-isoprene copolymers, polyethylene, polyisobutylene, polyvinylacetate and copolymers of vinyl acetate.

In embodiments of the invention, the chewing gum includes an edible acid and an effective amount of a sweetener as an anti-irritant. The acid is combined with the chewing gum base in an amount to adjust the pH in the mount to about 2.0 to 6.0 and preferably about 2.0 to 5.0. The anti-irritant is combined with the chewing gum base in an effective amount to mask the sour taste of the acid and to provide an anti-irritant effect. Generally, the anti-irritant is an artificial sweetener included in an amount of about 10% to 20% by weight based on the weight of the gum base.

In a further embodiment of the invention, the composition includes a water soluble base, an acidic component, bioactive agent and an anti-irritant in an effective amount to inhibit irritation caused by the acidic component and the bioactive agent. Typically, the composition is a tablet that can dissolve quickly in water. Preferably, the acidic component included in an effective amount to produce a pH of about 2.0 to 5.0 and includes an artificial sweetener in an amount to inhibit irritation caused by the acid. One example of soluble tablets contains sodium bicarbonate, citric acid, an analgesic, such as aspirin, and saccharine. In one embodiment, the composition contains an acid in an amount to form a solution of about pH 2.0 to 4.0.

The following non-limiting examples of the invention demonstrate various embodiments of the invention.

EXAMPLE 1

This example demonstrates that sodium saccharine and sucrose have little effect on the pH of an aqueous composition of the invention. In this example, the samples 1–6 were prepared from fresh lemon juice which was filtered to remove the pulp and other solid materials. Sample 1 was plain lemon juice with no sweeteners or additives. Samples 2–4 contained 3.0 ml lemon juice and sodium saccharine obtained under the trademark Sweet-N-Low in the amounts indicated in Table 1. Sample 5 contained 3.0 ml lemon juice and sucrose obtained as table sugar. Sample 6 was obtained by combining Samples 4 and 5 together. The proportions of the components and the resulting pH are indicated in Table 1 below.

TABLE 1

| Sample No. | Vol. of Lemon Juice | Anti-Irritant | pH |
|---|---|---|---|
| 1 | 3.0 ml | none | 2.36 |
| 2 | 3.0 ml | 1.0699 g saccharine | 2.25 |
| 3 | 3.0 ml | 1.9066 g saccharine | 2.23 |
| 4 | 3.0 ml | 2.888 g saccharine | 2.35 |

TABLE 1-continued

| Sample No. | Vol. of Lemon Juice | Anti-Irritant | pH |
|---|---|---|---|
| 5 | 3.0 ml | 3.3254 g sugar | 2.17 |
| 6 | 3.0 ml | 3.3254 g sugar 2.888 g saccharine | 2.24 |

The data demonstrates that the addition of saccharine and sucrose to lemon juice does not significantly change the pH. The pH of each sample was measured at 25° C. from two to six times to obtain a constant measurement. The pH meter was calibrated the measurement of each sample. The saccharine of samples 4 and 6 did not completely dissolve and were presumed to be saturated solutions.

EXAMPLE 2

An oral composition was prepared from 3.0 ml of fresh lemon juice and 1.0 gram of non-nutritive sweetener containing saccharine obtained under the trademark Sweet-N-Low. An adult male subject having calculus deposits on the subgingival and supragingival tooth surfaces applied the composition once every two days using a small proxy brush for inserting between the teeth followed by rinsing with the oral composition. The patient reported no irritation, burning or discomfort to the gum surfaces or to the teeth normally associated with an acidic solution when applied to the gums and tooth surfaces. After two weeks, significant reduction in the calculus depositions on the teeth were observed and the remaining calculus deposits easily separated from the tooth surface by the use of a dental tool.

EXAMPLE 3

A topical composition was prepared from about 3.0 ml fresh lemon juice and 1.0 g of a sweetener containing sodium saccharine obtained under the trademark Sweet-N-Low. The resulting solution was applied to a scratch on the skin of an adult male patient. The patient reported substantially no irritation or burning of the scratch.

EXAMPLE 4

The composition of Example 3 was applied to the surface of the eye of an adult male patient. The patient reported no burning or irritation in the eye.

EXAMPLE 5

A composition can be prepared from a chewing gum base, ascorbic acid as an active component, and sodium saccharine as an anti-irritant. The composition contains about 5.0% by weight ascorbic acid and about 10.0% by weight sodium saccharine based on the weight of the composition. The composition is administered by chewing to disperse the ascorbic acid and sodium saccharine to the surfaces of the patient's teeth for sufficient to treat the tooth surfaces. The ascorbic acid and the chewing action assist in removing calculus deposits from the tooth surfaces while the sodium saccharine provides an anti-irritant effect on the tooth and gum surfaces.

EXAMPLE 6

A composition is prepared from a sorbitol base to form a hard candy. The composition contains about 5.0% citric acid, acetic acid, ascorbic acid and mixtures thereof in an amount to adjust the pH of the saliva to about pH 4.0 to 6.0 when placed in the mouth. The composition also contains about 10.0% by weight sodium saccharine based on the weight of the composition to inhibit irritation to the tooth and gum surfaces. The composition is administered by placing in the mouth to dissolve the carrier and disperse the acid and anti-irritant. The carrier dissolves at a rate to provide a sustained release of the active component and anti-irritant.

EXAMPLE 7

A tablet is prepared from sorbitol as a carrier material, aspirin and about 10% by weight sodium saccharine. The tablet is administered orally and is swallowed whole by the patient to administer the aspirin to the patient. The patient experiences less stomach irritation than that experienced by patients when the anti-irritant is not used.

While various embodiments have been chosen to illustrate the invention, it will be understood by those skilled in the art that various modifications can be made without departing from the spirit and scope of the invention as defined in the following claims.

What is claimed is:

1. A process for treating irritated tissue to temporarily suppress pain receptors and inhibit pain and irritation of the tissue of an animal in need thereof, comprising the steps of:
   providing a composition comprising a solid carrier, at least one bioactive agent and at least one anti-irritant, said anti-irritant being a natural sweetener or non-nutritive sweetener in an effective amount to suppress the pain receptors of the tissue and to reduce pain and irritation to the tissue caused by said composition, and
   contacting said irritated tissue and body fluids of said irritated tissue with said composition to disperse said bioactive agent and anti-irritant in an amount to treat said tissue with said bioactive agent substantially without irritation to said tissue.

2. The process of claim 1, wherein said carrier is water soluble.

3. The process of claim 1, wherein said tissue is in the mouth of a patient and said process comprises placing said composition in the mouth of said patient.

4. The process of claim 1, wherein said composition further comprises an acid in an amount to form a solution having a pH of less than 6.0.

5. The process of claim 1, wherein said composition includes at least one acid to form a pH of about 2.0 to about 5.0.

6. The process of claim 4, wherein said acid is selected from the group consisting of citric acid, acetic acid, malic acid, adipic acid, fumaric acid, ascorbic acid, and mixtures thereof.

7. The process of claim 4, wherein said carrier is a water soluble solid and said composition comprises ascorbic and citric acid in an amount to form a solution having a pH of less than about 4.0 and said sweetener is saccharin in an amount to suppress pain receptors temporarily on the tissue being treated.

8. The process of claim 1, wherein said at least one bioactive compound is a pharmaceutically active compound selected from the group consisting of analgesics, antibiotics, antibacterial agents, anti-inflammatory agents, antifungals, immuno-suppressive agents, and mixtures thereof.

9. The process of claim 1, wherein said carrier is a chewing gum base.

10. The process of claim 1, wherein said sweetener is selected from the group consisting of saccharin, aspartame, cyclamates, and salts thereof.

11. The process of claim 10, wherein said composition comprises at least about 10% by of said sweetener.

12. The process of claim 1, wherein said composition further comprises an alkaline agent.

* * * * *